United States Patent [19]

Estell

[11] Patent Number: 5,039,446

[45] Date of Patent: Aug. 13, 1991

[54] LIQUID DETERGENT WITH STABILIZED ENZYME

[75] Inventor: David A. Estell, Mountain View, Calif.

[73] Assignee: Genencor International, Inc., Rochester, N.Y.

[21] Appl. No.: 559,456

[22] Filed: Jul. 23, 1990

Related U.S. Application Data

[63] Continuation of Ser. No. 214,558, Jul. 1, 1988, abandoned, which is a continuation of Ser. No. 75,373, Jul. 20, 1987, abandoned.

[51] Int. Cl.[5] .......................... C11D 1/00; C11D 9/60; C12N 9/96

[52] U.S. Cl. ...................... 252/174.12; 252/DIG. 12; 252/DIG. 4; 435/188

[58] Field of Search .................. 252/174.12, DIG. 12, 252/DIG. 4; 435/188

[56] References Cited

U.S. PATENT DOCUMENTS 4,566,985 1/1986 Bruno ............................ 252/174.12

FOREIGN PATENT DOCUMENTS 0199405 10/1986 European Pat. Off. .

OTHER PUBLICATIONS

Lindquist, R. N. and Terry, C., "Inhibition of Subtilisin by Boronic Acids, Potential Analogs of Tetrahedral Reaction Intermediates", *Archives of Biochemistry and Biophysics,* vol. 160 (1974), pp. 135-144, QP501A 77.

C. Abstracts I:85:1676s, *Cold Spring Harbor Conf. Cell Proliferation* 1975, 2 (Proteases Biol. Control), 429-54.

C. Abstracts II:74:94688h, *Proc. Nat. Acad. Sci. U.S.,* 1971, 68(2), 478-80.

*Primary Examiner*—Paul Lieberman

*Assistant Examiner*—Kevin D. McCarthy

*Attorney, Agent, or Firm*—James G. Passé

[57] ABSTRACT

Liquid detergent containing enzymes particularly proteases are stabilized against enzyme degradation prior to use by inclusion of an inhibitor of the enzyme having a dissociation constant of between about $1\times10^{-2}$M and about $1\times10^{-7}$M which binds to the enzyme such that prior to use of the detergent at least about 55% of the enzyme is bound to the enzyme inhibitor essentially at the enzyme active site. Such enzyme inhibitor so selected can be used effectively in concentrations much lower than previously taught; i.e., from about 0.002% to less than 0.1% weight/weight.

8 Claims, No Drawings

LIQUID DETERGENT WITH STABILIZED ENZYME

This is a continuation of application Ser. No. 214,558 filed July 1, 1988, now abandoned, which is a continuation of application Ser. No. 075,373, filed July 20, 1987, abandoned.

BACKGROUND OF THE INVENTION

1. Field of the Invention

The present invention relates to enzyme compositions and liquid detergent compositions. Particularly, the invention relates to enzymes which have been stabilized and to liquid laundry detergents with the stabilized enzymes.

2. Background Art

The development of detergents for the cleaning of fabric have improved steadily over the recent past. Improvements in detergent additives have included improvements of surfactants, builders, dispersing agents, fluorescent whitening agents, bleaching agents, etc. and have allowed detergents to be formulated into powders, granules and liquids. See e.g., detergents composition in U.S. Pat. Nos. 3,551,002, 3,558,498, 3,623,957, 3,749,671, 3,790,482, 3,985,686, 4,090,973, 4,011,169, 4,111,855, 4,142,999, 4,242,219, 4,261,868, 4,318,818, 4,404,115, and 4,381,247 incorporated herein by reference. Detergents compositions often contain enzymes (e.g., a protease) to aid in the degradation and removal of enzyme sensitive stains, soils and deposits. Detergent formulations which contain enzymes, however, experience the problem of decreased enzyme activity over time, especially liquid detergents which contain high levels of surfactant and water. Enzymes may hydrolyze in water and often a protease will degrade itself or other enzymes that may be present. Surfactants, for example alkyl sulfates, tend to deactivate enzymes and render them inactive. Detergent builders can sequester the calcium ion needed for enzyme stability. These problems require either an expiration date on the detergent or the undesirable alternative of an increased amount of costly enzyme being added to the detergent. There is a continuing need, therefore, for liquid detergents which contain enzymes which are stabilized and exhibit a greater activity over time. The prior art has attempted to deal with these problems.

Meister, U.S. Pat. No. 3,095,358, utilizes sorbitol to stabilize aqueous solutions containing enzymes such as papain and mixtures of protease and amylase obtained from Bacillus subtilis. This method also requires large amounts of stabilizing agent. Several patents list compounds which stabilize enzymes. However, none of the following are competitive inhibitors.

Cayle, U.S. Pat. No. 3,296,094, utilizes partially hydrolyzed and solubilized collagen and glycerol to stabilize aqueous solutions of proteolytic enzymes. This method requires large quantities of glycerol by weight of the total solution and, therefore, adds significantly to the cost of the enzyme solution.

McCarty, U.S. Pat. No. 3,557,002, uses short chain alkyl or alkoxy alkyl monohydroxy alcohols to stabilized enzyme preparations. These preparations will protect the listed enzymes at at least 50% enzyme activity after storage at 100° F. for 5 weeks. Diehl, U.S. Pat. No. 4,011,169, uses aminated polysaccharides such as aminated cellulose to stabilize enzymatic activity. In U.S. Pat. No. 4,142,999, Bloching uses mono and polyvalent alcohols and ethers thereof, and an effective amount of an alkoxylated alkylamine to stabilize enzyme activity.

U.S. Pat. No. 4,261,868, Hora et al, issued Apr. 14, 1981, discloses liquid detergents containing enzymes and, as an enzyme-stabilizing system, 2–25% of a polyfunctional amino compound selected from diethanolamine, triethanolamine, diisopropanolamine, triisopropanolimine and tris(hydroxymethyl) aminomethane, and 0.25–15% of a boron compound selected from boric acid, boric oxide, borax, and sodium ortho, meta and pyroborate. The compositions can contain 10–60% surfactant, including anionics, and up to 40% builder.

U.S. Pat. No. 4,318,818, Letton et al, issued Mar. 9, 1982, discloses liquid detergents containing enzymes and an enzyme-stabilizing system comprising calcium ion and a low molecular weight carboxylic acid or salt, preferably a formate. The compositions preferably contain from about 20% to 50% surfactant, which can be anionic. In a preferred embodiment, the compositions contain about 3% to 15% of a saturated fatty acid. They are otherwise substantially free of builders, but can contain minor amounts of sequestrants.

U.S. Pat. No. 4,404,115, Tai, issued Sept. 13, 1983, discloses liquid cleaning compositions, preferably built liquid detergents, containing enzyme, 1–15% alkali metal pentaborate, 0–15% alkali metal sulfite, and 0–15% of a polyol having 2–6 hydroxy groups. The compositions can contain 1–60% surfactant, preferably a mixture of anionic and non-ionic in a weight ratio of 6:1 to 1:1, with or without soap. The compositions also preferably contain 5–50% builder.

European Patent Application 0,130,756, published Jan. 9, 1985, discloses proteolytic enzymes useful herein and methods for their preparation. The enzymes are said to be useful in laundry detergents, both liquid and granular. They can be combined with surfactants (including anionics), builders, bleach and/or fluorescent whitening agents, but there is no disclosure of specific detergent compositions.

European Patent Application 0,199,405 published Oct. 10, 1986 discloses liquid detergent compositions containing synthetic surfactants, an enzyme and boric acid or boron compound from about 0.1% to about 10%, preferably from 0.25% to 5%, and most preferably from about 0.5% to about 3%. No disclosure is made, however, of how to match the enzyme with the boric acid. As a percentage of the enzyme, the boric acid represents at least 2% up to 100,000%.

The art is illustrative of the cost and expense that has gone into stabilization of enzymes by way of adding large amounts of additional ingredients as well as the difficulties in dilution which occur due to varying teachings of the amounts of stabilizing agent which must be added based on the amount of water and other ingredient present.

It is an object of the invention therefore to stabilize enzymes and enzymes in liquid detergents with a minimum standardized amount of a stabilizer in the presence of water, detergents or other, if any, ingredients present in the liquid detergent.

SUMMARY OF THE INVENTION

In accordance therewith it has been discovered that enzymes can be stabilized against such problems. The invention relates to a liquid detergent composition comprising:

a) from about 1% to about 75% of a surfactant;

b) from about 10% to about 95% of water by weight;

c) from about 0.01% to about 5% of an enzyme suitable for use in detergent compositions; and d) from about 0.002% to less than 0.1% of an enzyme inhibitor selected at a concentration of at least about 70% of the amount of enzyme present in the composition on a molar basis and having an inhibition constant of from about $1\times10^{-2}M$ to about $1\times10^{-7}M$ wherein at least about 55% of the enzyme is bound to the enzyme inhibitor essentially at the enzyme active site on a molar basis and that the remaining unbound enzyme is in its free form and wherein upon dilution of the composition to between 2 and 10,000 times, less than about 45% of the enzyme is bound to the enzyme inhibitor on a molar basis and that the remaining enzyme is in its free form.

The invention also relates to a stabliized enzyme composition comprising:

a) an enzyme suitable for use in detergent compositions; and b) from about 0.04% to less than about 2% of an enzyme inhibitor selected at a concentration of at least about 70% of the amount of enzyme present in the composition on a molar basis and having an inhibition constant of from about $1\times10^{-2}M$ to about $1\times10^{-7}M$ wherein at least about 55% of the enzyme is bound to the enzyme inhibitor essentially at the enzyme active site on a molar basis and that the remaining unbound enzyme is in its free form and wherein upon dilution of the composition to between 2 and 100,000 times, less than about 45% of the enzyme is bound to the enzyme inhibitor on a molar basis and that the remaining enzyme is in its free form.

DETAILED DESCRIPTION OF THE INVENTION

Basic liquid detergent compositions contain a surfactant, preferably a non-ionic or anionic surfactant and from about 10% to about 95% water on a weight basis in addition to the enzyme and enzyme inhibitor. Varying amounts of stabilizers have been taught, but in general the inhibitor is taught to be at least 0.1% of the detergent composition.

The preferred compositions of the present invention contain from about 1% to about 75%, preferably from about 10% to about 40% and most preferably from about 15% to about 30%, by weight of a surfactant. Suitable anionic synthetic surfactants are disclosed in U.S. Pat. No. 4,111,855, Barrat et al, issued Aug. 25, 1981, and in U.S. Pat. No. 3,929,678, Laughlin et al, issued Dec. 30, 1975, both incorporated herein by reference.

Useful anionic surfactants also include the water-soluble salts, particularly the alkali metal, ammonium and alkylolammonium (e.g., monoethanolammonium or triethanolammonium) salts, of organic sulfuric reaction products having in their molecular structure an alkyl group containing from about 10 to about 20 carbon atoms and a sulfonic acid or sulfuric acid ester group. (Included in the term "alkyl" is the alkyl portion of aryl groups.) Examples of this group of synthetic surfactants are the alkyl sulfates, especially those obtained by sulfating the higher alcohols ($C_8$–$C_{18}$ carbon atoms) such as those produced by reducing the glycerides of tallow or coconut oil; and the alkylbenzene sulfonates in which the alkyl group contains from about 9 to 15 carbon atoms, in straight chain or branched chain configuration, e.g., those of the type described in U.S. Pat. Nos. 2,220,099 and 2,477,383. Especially valuable are linear straight chain alkylbenzene sulfonates in which the average number of carbon atoms in the alkyl group is from about 11 to 14.

Other anionic surfactants herein are the water-soluble salts of: paraffin sulfonates containing from about 8 to about 24 (preferably about 12 to 18) carbon atoms; alkyl glyceryl ether sulfonates, especially those ethers of $C_{8-18}$ alcohols (e.g., those derived from tallow and coconut oil); alkyl phenol ethylene oxide ether sulfates containing from about 1 to about 4 units of ethylene oxide per molecule and from about 8 to about 12 carbon atoms in the alkyl group; and alkyl ethylene oxide ether sulfates containing about 1 to about 4 units of ethylene oxide per molecule and from about 10 to about 20 carbon atoms in the alkyl group.

Other useful anionic surfactants include the water-soluble salts of esters of alpha-sulfonated fatty acids containing from about 6 to 20 carbon atoms in the fatty acid group and from about 1 to 10 carbon atoms in the ester group: water-soluble salts of 2-acyloxy-alkane-1-sulfonic acids containing from about 2 to 9 carbon atoms in the acyl group and from about 9 to about 23 carbon atoms in the alkane moiety; water-soluble salts of olefin sulfonates containing from about 12 to 24 carbon atoms; and beta-alkyloxy alkane sulfonates containing from about 1 to 3 carbon atoms in the alkyl group and from about 8 to 20 carbon atoms in the alkane moiety.

Preferred anionic surfactants are the $C_{11}$–$C_{13}$ linear alkylbenzene sulfonates, and mixtures thereof.

The compositions preferably contain from about 1% to about 5%, more preferably from about 2% to about 4%, by weight of unethoxylated alkyl sulfate. These alkyl sulfates are desired for best detergency performance, in part because they are very denaturing to stains.

The composition herein can optionally contain other synthetic surfactants known in the art, such as the non-ionic, cationic, zwitterionic, and ampholytic surfactants described in the above-cited Barrat et al and Laughlin et al patents.

A preferred cosurfactant, used at a level of from about 1% to about 25% preferably from about 3% to about 15%, by weight of the composition, is an ethoxylated non-ionic surfactant of the formula $R^1(OC_2H_4)_nOH$, wherein $R^1$ is a $C_{10}$–$C_{16}$ alkyl group or a $C_8$–$C_{12}$ alkyl phenyl group, n is from about 3 to about 9, and said non-ionic surfactant has an HLB (hydrophile-lipophile balance) of from about 6 to about 14, preferably from about 10 to about 13. These surfactants are more fully described in U.S. Pat. Nos. 4,285,841, Barrat et al, issued Aug. 25, 1981, and 4,284,532, Leikhim et al, issue Aug. 18, 1981, both incorporated herein by reference. Particularly preferred are condensation products of $C_{12}$–$C_{15}$ alcohols with from about 3 to about 8 moles of ethylene oxide per mole of alcohol, e.g., $C_{12}$–$C_{13}$ alcohol condensed with about 6.5 moles of ethylene oxide per mole of alcohol.

Preferred cosurfactants for use with the above ethoxylated non-ionic surfactants are amides of the formula

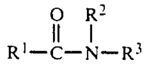

wherein $R^1$ is an alkyl, hydroxyalkyl or alkenyl radical containing from about 8 to about carbon atoms, and $R^2$ and $R^3$ are selected from the group consisting of hydrogen, methyl, ethyl, propyl, isopropyl, 2-hydroxyethyl, 2-hydroxypropyl, 3-hydroxypropyl, and said radicals additionally containing up to about 5 ethylene oxide units, provided at least one of $R^2$ and $R^3$ contains a hydroxyl group.

Preferred amides are the $C_8$-$C_{20}$ fatty acid alkylol amides in which each alkylol group contains from 1 to 3 carbon atoms, and additionally can contain up to about 2 ethylene oxide units. Particularly preferred are the $C_{12}$-$C_{16}$ fatty acid monoethanol and diethanol amides.

Certain compositions herein preferably contain from about 5% to about 20%, preferably from about 6% to about 15%, more preferably from about 7% to about 12%, by weight of a mixture of the above ethoxylated non-ionic surfactant and amide surfactant in a weight ratio of from about 4:1 to 1:4, preferably from about 3:1 to about 1:3, more preferably from about 2:1 to about 1:2. In addition, the weight ratio of anionic synthetic surfactant (on an acid basis) to the total non-ionic surfactant (both the ethoxylated non-ionic and the amide) should be from about 2:1 to about 4:1, preferably from about 2.5:1 to about 3.5:1, to ensure the formation and adsorption of sufficient hardness surfactants at the oil/water interface to provide good greasy/oily soil removal.

Other preferred cosurfactants, used at a level of from about 0.5% to about 3%, preferably from about 0.7% to about 2%, by weight are the quaternary ammonium, amine or amine oxide surfactants described in U.S. Pat. No. 4,507,219, Hughes, issued Mar. 26, 1985, incorporated herein, by reference.

While the compositions herein can contain di-long chain quaternary ammonium cationic surfactants (e.g., those having 2 chains, each containing an average of from about 16 to about 22 chains, each containing an average of from about 16 to about 22 carbon atoms), such as disclosed in British Patent 2,041,968, Murphy, published Sept. 19, 1979, incorporated herein by reference, the compositions preferably contain less than about 2%, more preferably less than about 1%, by weight of such surfactants. Most preferably, the compositions are substantially free of such surfactants because they appear to be detrimental to the stability of the enzymes herein.

The compositions herein optionally contain from about 5% to about 40%, preferably from about 8% to about 30%, more preferably from about 10% to about 25%, by weight of a detergent builder material. In addition, the composition should contain at least about 20%, preferably from about 25% to about 60%, more preferably from about 30% to about 50%, by weight of the anionic synthetic surfactant and builder.

Useful builders are fatty acids containing from about 10 to about 22 carbon atoms. Preferred are saturated fatty acids containing from about t10 to about 18, preferably from about 10 to about 14, carbon atoms. When present, the fatty acid preferably represents about 5% to about 20%, more preferably from about 8% to about 16%, by weight of the composition.

Suitable saturated fatty acids can be obtained from natural sources such as plant or animal esters (e.g., palm kernel oil, palm oil and coconut oil) or synthetically prepared (e.g., via the oxidation of petroleum or by hydrogenation of carbon monoxide via the Fister-Tropsch process). Examples of suitable saturated fatty acids for use in the compositions of this invention include capric, lauric, myristic, coconut an palm kernel fatty acid. Preferred are saturated coconut fatty acids from about 5:1 to 1:1 (preferably about 3:1) weight ratio mixtures of lauric an myristic acid; mixtures of the above with minor amounts (e.g., 1%-30% of total fatty acid) of oleic acid; and palm kernel fatty acid.

Detergent builders useful herein also include the polycarboxylate, polyphosphonate and polyphosphate builders described in U.S. Pat. No. 4,284,532, Leikhim et al, issued Aug. 18, 1981, incorporated herein by reference. water-soluble polycarboxylate builders, particularly citrates, are preferred of this group. Polycarboxylate builder preferably represent from about 1% to about 20% by weight of the composition.

Suitable polycarboxylate builder include the various aminopolycarboxylates, cycloalkane polycarboxylates, ether polycarboxylates, alkyl polycarboxylates, epoxy polycarboxylates, tetrahydrofuran polycarboxylates, benzene polycarboxylates, and polyacetal polycarboxylates.

Examples of such polycarboxylate builders are sodium and potassium ethylenediaminetetraacetate; sodium and potassium nitrilotriacetate; the water-soluble salts of phytic acid, e.g., sodium and potassium phytates, disclose in U.S. Pat. No. 1,739,942, Eckey, issued Mar. 27, 1956, incorporated herein by reference; the polycarboxylate materials described in U.S. Pat. No. 3,364,103, incorporated herein by reference.

Useful detergent builders also include the water-soluble salts of polymeric aliphatic polycarboxylic acids having the following structural and physical characteristics: (a) a minimum molecular weight of about 350 calculated as to the acid form; (b) an equivalent weight of about 50 to about 80 calculated as to acid form; (3) at least 45 mole percent of the monomeric species having at least two carboxyl radicals separated from each other by not more than two carbon atoms; (d) the site of attachment of the polymer chain of any carboxyl-containing radical being separated by not more than three carbon atoms along the polymer chain from the site of attachment of the next carboxyl-containing radical. Specific examples of such builders are the polymers and copolymers of itaconic acid, aconitic acid maleic acid, mesaconic acid, fumaric acid, methylene malonic acid, and citraconic acid.

Other suitable polycarboxylate builders include the water-soluble salts, especially the sodium and potassium salts, of mellitic acid, citric acid, pyromellitic acid, benzene pentacarboxylic acid, oxydiacetic acid, carboxymethyloxysuccinic acid, carboxmethyloxymalonic acid, cis-cyclohexanehexacarboxylic acid, cis-cyclopentanetetracarboxylic acid and oxydisuccinic acid.

Other polycarboxylates for use herein are the polyacetal carboxylates described in U.S. Pat. No. 4,144,226, issued Mar. 13, 1979 to Crutchfield et al, and U.S. Pat. No. 4,146,495, issued Mar. 27, 1979 to Crutchfield et al, both incorporated herein by reference.

Other detergent builders useful herein include the aluminosilicate ion exchange material described in U.S. Pat. No. 4,405,483, Kuzel et al, issued Sept. 20, 1983, incorporated herein by reference.

As part of the builder system, the compositions herein preferably contain from about 0.1% to about 1%, more preferably from about 0.2% to about 0.6%, by weight of water-soluble salts of ethylenediamine tetramethylenephosphonic acid, diethylenetriamine pentamethylenephosphonic acid, ethylenediamine tetraacetic acid, or diethylenetriamine pentaacetic acid to enhance cleaning performance when pretreating fabrics.

Enzymes for inclusion in liquid detergent compositions of the invention are those suitable for use in detergent compositions and are well known in the art as discussed above. The preferred enzymes are proteases such as subtilisin, and amylases such as those from bacillus species. Preferred proteases are also those described in European Patent Applications 130,756 published Jan. 9, 1985, and incorporated herein by reference. One or more enzyme may be included in the composition.

The above enzyme is preferably included in an amount sufficient to provide an activity of from about 0.001 to about 0.1, more preferably from about 0.005 to about 0.07, most preferably from about 0.01 to about 0.04, Ansorr units per gram of composition. On a percentage basis of the composition, it is preferable that it be from about 0.01% to about 5% by weight of the liquid detergent composition. The enzymes herein are preferably purified, prior to incorporation in the finished composition, so that they have no detectable order at a concentration of less than about 0.002 Anson units per gram in distilled water. They preferably have no detectable order at a concentration of less than about 0.0025, more preferably less than about 0.003, Anson units per gram of distilled water.

The compositions herein have an initial pH of from about 6.5 to about 9.5, preferably from about 7 to about 8.5, most preferably from about 7.2 to about 8.0, at a concentration of 0.2% by weight in distilled water at 20° C. Preferred pH buffers include monethanolamine and triethanolamine. Monethanolamine and triethanolamine also further enhance enzyme stability, and preferably are included at levels of from about 0.5% to about 10%, preferably from about 1% to about 4%, by weight of the composition.

Other optional components for use in the liquid detergents herein include soil removal agents, antiredeposition agents, suds regulants, hydrotropes, opacifiers, antioxidants, bactericides, dyes, perfumes, and brighteners known in the art. Such optional components generally represent less than about 15%, preferably from about 1% to about 10%, by weight of the composition.

The enzyme inhibitor of the invention is selected to be a competitive inhibitor of the selected enzyme. By specifically selecting a competitive inhibitor as follows, substantially less enzyme can be used: the enzyme inhibitor of the invention is a composition having a inhibition constant ($K_I$) of from about $1\times10^2$M to about $1\times10^7$M and preferably from about $10^3$ to $10^4$M. The enzyme inhibitor is chosen in an amount at least about 70 percent on a molar basis of the enzyme be stabilized preferably at least 80% to about 100% and proportional to the inhibition constant such that at least about 55% of the enzyme is essentially bound to the enzyme inhibitor at the active site of the enzyme to an extent that the remaining unbound enzyme is in its free form in the composition yet a dilution of the liquid detergent composition with water or other appropriate liquid of from about 2 to about 10,000 times or a dilution of the enzyme composition with water detergent, or other appropriate liquid from about 2 to about 100,000 times, less than about 45% of the enzyme is bound to the enzyme inhibitor on a molar basis such that the remaining enzyme is in its free form. Enzyme Inhibitor Complex (EI) can be calculated by the formula:

$$EI = \frac{(Et + It + Ki - \sqrt{(Et + It + Ki)^2 - 4(Et)(It)}}{2}$$

Wherein it is total Inhibitor concentration on a molar basis and Et is Total Enzyme concentration on a molar basis.

As a percentage by weight of liquid detergent, the enzyme inhibitor should be less than 0.1% but at least about 0.002%, and preferably from 0.004% to 0.05%. As a percentage by weight of the enzyme, the enzyme inhibitor should be from about 0.04% to less than about 2% of the enzyme and preferably from 0.08% to 1%.

So, for example, phenylboronic acid (PBA, $K_I=2.3\times10^4$M) can be used as an inhibitor for subtilisin. Other examples of enzyme/enzyme inhibitor combinations include subtilisin and either butane boronic acid ($K_I=7.2\times10^3$M) or leupeptin ($K_I=1.6\times10^4$M). One skilled in the art would be able to pair other enzymes and enzyme inhibitors together and the disclosure is intended to include such combinations herein.

Finally, the liquid detergent compositions herein contain from about 10% to about 95%, preferably from about 20% to about 70%, and more preferably from about 30% to about 50% by weight of water.

The composition of the invention may contain other enzymes which do not have corresponding competitive inhibitors. In such instances where the stabilized enzyme is a protease such enzymes will be partially stabilized against the enzymatic degradation of the proteases.

One skilled in the art would then be able to make the stabilized enzyme compositions merely by admixing the selected ingredients or the like. One would then be free to add the composition to detergent compositions as described above. While the enzymes described are all primarily for use in detergent applications, such enzymes could also have other uses, e.g., contact lens cleaning or bleaching, and the stabilized enzyme compositions can be used therein.

DESCRIPTION OF THE PREFERRED EMBODIMENTS

The following examples are illustrative and are not intended to limit the invention. One skilled in the art would be able to substitute enzymes and enzyme inhibitors based on the disclosure herein without undue experimentation or deviation from the spirit or scope of the claims.

EXAMPLE 1

The following table shows the results of several incubations of subtilisin(E) with or without Phenylboric acid (PBA or I) at pH 7.5 and 37 degrees celsius. The data show that PBA is a very effective agent for stabilization of subtilisin even in the presence of 10 mm EDTA. In the concentrated stocks between 97 and 99.5% of the enzyme is inactive but upon a 1:500 dilution in the absence of substrate (e.g. stain or synthetic substrate are for measurement purposes), about 74 to about 93% of the enzyme is active.

Enzyme activity was measured after a 1:500 dilution by following the hydrolysis of the substrate succinyl-L-Ala-L-Ala-L-Pro-L-Phe-P-nitroanilide. The reaction was monitored by following the release of p-nitroaniline spectrophotometrically at 410 nm. One unit of activity is defined as the amount of enzyme that produces A410/min of 1.0 at 25'C. in 0.1M Tris pH 8.6, $3\times10^4$M substrate.

PERCENT ACTIVITY AS A FUNCTION OF INCUBATION TIME AT 37° C.

| TIME | 1 (E) | 2 (E + I) | 3 (E + EDTA) | 4 (E + EDTA + I) | 5 (E + Ca) | 6 (E + Ca + I) |
|---|---|---|---|---|---|---|
| 0 | 100 | 100 | 100 | 100 | 100 | 100 |
| 3.5 h | 70 | 91 | 20 | 98 | 90 | 126 |
| 6.0 h | 48 | 90 | 7 | 82 | 75 | 125 |
| 75.0 h | 11 | 103 | 0 | 16 | 22 | 123 |

| TIME | 7 (E + EDTA) | 8 (E + EDTA + I (.008M)) | 9 (E + EDTA + I (.04M)) [11% TW-80] |
|---|---|---|---|
| 0 | 100 | 100 | 100 |
| 5.5 h | 23 | 57 | 79 |
| 22.0 h | 2 | 17 | 44 |

| TIME | 10 (E + EDTA) | 11 (E + EDTA + I) [35% NP-40, 1% NaBorate] |
|---|---|---|
| 0 | 100 | 100 |
| 2.0 h | 83 | 112 |
| 3.5 h | 67 | 102 |
| 6.0 h | 57 | 97 |
| 20.5 h | 13 | 61 |

INCUBATIONS
1 1.3 mg/ml subtilisin
2 1.3 mg/ml subtilisin, 20 mM PBA
3 1.3 mg/ml subtilisin, 2.5 mM EDTA
4 1.3 mg/ml subtilisin, 2.5 mM EDTA, 20 mM PBA
5 1.3 mg/ml subtilisin, 10 mM Ca
6 1.3 mg/ml subtilisin, 10 mM, 10 mM PBA
7 1.3 mg/ml subtilisin, 10 mM EDTA, 22% Tween 80
8 1.3 mg/ml subtilisin, 10 mM EDTA, 22% Tween 80, 8 mM PBA
9 1.3 mg/ml subtilisin, 10 mM EDTA, 22% Tween 80, 40 mM PBA
10 1.0 mg/ml subtilisin, 10 mM EDTA, 50 mM NaBorate, 35% NP-40
11 1.0 mg/ml subtilisin, 10 mM EDTA, 50 mM NaBorate, 35% NP-40, 40 mM PBA

EXAMPLE 2

Three inhibitors of subtillsin were tested to show that the stabilization is a function of the inhibition constant and therefore the stabilizing agent is bound to the enzyme rather than free stabilizer as in the prior art.

Solutions of Phenyl boronic acid (PB) ($K_I=1.6\times10^{-4}$M), Leupeptin (LP) ($K_I=2.3\times10^{-4}$M), and butane boronic acid (BB) ($K_I=7.2\times10^{-3}$M)[1] were made in 1, 10 and 100 times the $K_I$ as follows:

| LP100 | LP10 | LP1 |
|---|---|---|
| 500 μl LP ($3.2\times10^{-2}$M) | 50 μl LP | 5 μl LP |
| 10 μl 250 nM EDTA | 10 μl EDTA | 10 μl EDTA |
| 30 μl Subtilisin (25 mg/ml) | 30 μl Subtilisin | 30 μl Subt |
| 460 μl 0.1M MOPS, | 910 μl M7.5 | 955 μl M7.5 |

pH 7.5 (M7.5)

| PB100 | PB10 | PB1 |
|---|---|---|
| 500 μl PB ($4.6\times10^{-2}$M) | 50 μl PB | 5 μl PB |
| 10 μl EDTA | 10 μl EDTA | 10 μl EDTA |
| 30 μl Subt. | 30 μl Subt. | 30 μl Subt. |
| 460 μl M7.5 | 910 μl M7.5 | 955 μl M7.5 |

-continued

| BB10 | BB1 |
|---|---|
| 500 μl BB ($1.4\times10^{-1}$M) | 50 μl BB |
| 10 μl EDTA | 10 μl EDTA |
| 30 μl Subt | 30 μl Subt. |
| 460 μl M7.5 | 910 μl M7.5 |
| Control | |
| 10 μl EDTA | |
| 30 μl Subt. | |
| 960 μl M7.5 | |

[1]Philipp, M. and Bender, M. L. Molecular and Cellular Biochemistry, 51, 5-32 (1983).

The following inhibitor concentrations were calculated:

| | | | |
|---|---|---|---|
| [$1.6\times10^{-2}$M] LP100 | [$2.3\times10^{-2}$M] PB100 | [$1.6\times10^{-3}$M] LP10 | [$2.3\times10^{-3}$M] BP10 |
| [$7.2\times10^{-2}$M] BB10 | [$1.6\times10^{-4}$M] LP1 | [$2.3\times10^{-4}$M] PB1 | [$7.2\times10^{-3}$M] BB1 |

The following relative enzyme activities were shown over time by following absorbance at 410 nanometers/-min. by the method of Example 1 with the following results.

| Time | LP100 | PB100 | LP10 | PB10 | BB10 | LP1 | PB1 | BB1 | Control |
|---|---|---|---|---|---|---|---|---|---|
| 0 | .82 | 1.05 | .92 | .957 | .946 | .89 | .93 | .865 | .942 |
| 2 hr | .736 | .864 | .704 | .751 | .665 | .422 | .536 | .409 | .403 |
| | (90%) | (82%) | (77%) | (78%) | (71%) | (47%) | (58%) | (47%) | (43%) |
| 4 hr | .662 | .777 | .518 | .587 | .422 | .174 | .264 | .189 | .15 |
| | (81%) | (74%) | (56%) | (61%) | (45%) | (20%) | (28%) | (22%) | (16%) |

These results clearly indicate that stabilization is dependent on the concentration of inhibitor relative to its $K_I$ and therefore results from enzyme inhibitor complex formation.

What is claimed is:

1. A liquid detergent composition comprising:

a) from about 1% to about 75% of a surfactant by weight of the composition;

b) from about 10% to about 95% of water by weight of the composition;

c) from about 0.01% to about 5% by weight of the composition of an enzyme suitable for use in detergent compositions for which leupeptin is a competitive inhibitor, included in an amount such that its activity is from about 0.001 to 0.1 Anson units per gram of composition.

d) from about 0.04% to less than about 2% of leupeptin by weight of the enzyme.

2. A liquid detergent according to claim 1 wherein the enzyme is a protease.

3. A liquid detergent according to claim 2 wherein the protease is a subtilisin.

4. A composition according to claim 1 wherein the enzyme is in a purified form.

5. A stabilized enzyme composition for inclusion in a liquid detergent comprising:

a) an enzyme suitable for use in detergent compositions for which leupeptin is a competitive inhibitor in a concentration such that upon addition to a liquid detergent composition it can be present in said detergent composition at from about 0.01% to about 5% by weight of the detergent composition such that its activity is from about 0.001 to 0.1 Anson units per gram of composition;

b) from about 0.04% to less than about 2% of leupeptin by weight of the enzyme.

6. An enzyme composition according to claim 5 which is a protease.

7. A protease according to claim 6 which is a subtilisin.

8. A composition according to claim 5 wherein the enzyme is in a purified form.

* * * * *